(12) United States Patent
Rosenfeld

(10) Patent No.: US 10,056,186 B2
(45) Date of Patent: Aug. 21, 2018

(54) METHODS AND APPARATUS FOR COLLOCATING ELECTROMAGNETIC COILS AND ELECTRONIC CIRCUITS

(71) Applicant: VAYYAR IMAGING LTD., Yehud (IL)

(72) Inventor: Jonathan Rosenfeld, Ramat Hasharon (IL)

(73) Assignee: VAYYAR IMAGING LTD, Yehud (IL)

( * ) Notice: Subject to any disclaimer, the term of this patent is extended or adjusted under 35 U.S.C. 154(b) by 0 days.

(21) Appl. No.: 15/360,350

(22) Filed: Nov. 23, 2016

(65) Prior Publication Data

US 2017/0148567 A1    May 25, 2017

Related U.S. Application Data

(60) Provisional application No. 62/259,661, filed on Nov. 25, 2015.

(51) Int. Cl.

| G01V 3/08 | (2006.01) |
|---|---|
| G01V 3/10 | (2006.01) |
| H01F 38/14 | (2006.01) |
| G01S 13/88 | (2006.01) |
| G01N 27/02 | (2006.01) |
| H05B 6/44 | (2006.01) |
| H02J 50/10 | (2016.01) |
| H01F 27/28 | (2006.01) |

(52) U.S. Cl.
CPC ........... *H01F 38/14* (2013.01); *G01N 27/025* (2013.01); *G01S 13/885* (2013.01); *G01V 3/08* (2013.01); *G01V 3/081* (2013.01); *G01V 3/10* (2013.01); *G01V 3/101* (2013.01); *G01V 3/102* (2013.01); *G01V 3/104* (2013.01); *G01V 3/105* (2013.01); *H01F 27/2804* (2013.01); *H02J 50/10* (2016.02); *H05B 6/44* (2013.01); *G01V 3/107* (2013.01)

(58) Field of Classification Search
CPC . G01V 3/08; G01V 3/081; G01V 3/10; G01V 3/101; G01V 3/102; G01V 3/104; G01V 3/105; G01V 3/107; G01V 3/108; G01V 3/15; G01V 3/16; G01V 3/165
USPC .................................. 324/67, 323, 326, 376
See application file for complete search history.

(56) References Cited

U.S. PATENT DOCUMENTS

| 2006/0052957 A1* | 3/2006 | Hidehira | ............ G01R 31/2806 702/58 |
| 2006/0081397 A1* | 4/2006 | Enchi | ..................... H05K 1/165 174/260 |

(Continued)

*Primary Examiner* — Huy Q Phan
*Assistant Examiner* — Raul Rios Russo
(74) *Attorney, Agent, or Firm* — Browdy and Neimark, PLLC

(57) ABSTRACT

Methods and apparatus according to the invention include inductive units or apparatus such as magnetic metal detectors comprising multiple electromagnetic coils and circuit boards such as electronic printed circuit boards (PCBs) so that the circuit boards, while containing metallic surfaces and layers, are positioned in such a way as to reduce or eliminate their effect on the metal detector's coils. The apparatus comprising: a plurality of electromagnetic coils and a plurality of circuit boards, and wherein at least one of said circuit boards is positioned so that its thickness direction is orthogonal to the magnetic field of at least one of said coils.

16 Claims, 5 Drawing Sheets

(56) References Cited

U.S. PATENT DOCUMENTS

| | | | |
|---|---|---|---|
| 2007/0007953 A1 | 1/2007 | Keene et al. | |
| 2008/0030415 A1* | 2/2008 | Homan | H01Q 1/04 |
| | | | 343/719 |
| 2011/0068795 A1 | 3/2011 | Duvoisin, III | |
| 2011/0241958 A1* | 10/2011 | Yosui | H01Q 1/2225 |
| | | | 343/788 |
| 2013/0113648 A1 | 5/2013 | Duvoisin, III et al. | |
| 2013/0134968 A1 | 5/2013 | Zibold et al. | |
| 2014/0125321 A1* | 5/2014 | Dames | G01R 15/181 |
| | | | 324/127 |
| 2014/0312891 A1* | 10/2014 | Micheau-Cunningham | G01N 27/904 |
| | | | 324/242 |
| 2018/0031646 A1* | 2/2018 | Tiernan | G01N 27/9033 |

* cited by examiner

METHODS AND APPARATUS FOR COLLOCATING ELECTROMAGNETIC COILS AND ELECTRONIC CIRCUITS

CROSS-REFERENCE

The present application claims the benefit of U.S. Provisional Application Ser. No. 62/259,661, filed on Nov. 25, 2015, entitled "METHODS AND APPARATUS FOR COLLOCATING ELECTROMAGNETIC COILS AND ELECTRONIC CIRUITS", the entire disclosure of which is incorporated herein by reference.

INCORPORATION BY REFERENCE

All publications, patents, and patent applications mentioned in this specification are herein incorporated by reference to the same extent as if each individual publication, patent, or patent application was specifically and individually indicated to be incorporated by reference.

FIELD OF THE INVENTION

The present invention relates to methods and apparatus for optimizing systems with electromagnetic coils and circuit boards such as metal detectors, and more specifically, but not exclusively, to methods and apparatus for optimizing the system's dynamic range and reducing interference.

BACKGROUND

Inductive systems such as metal detectors typically use magnetic effects such as the variation of mutual inductance in a multi coil system or the induced current on a single coil system resulted due to a presence of a metallic target.

The signal measured by a metal detector, for example, corresponds to an alteration in a magnetic field due to the presence of the metallic object to be detected, therefore, introducing additional components and/or systems with metallic content and or/circuitry has several adverse effects. One such effect is the lowering of the metal detection usable dynamic range—for example if one introduces a metallic element in the detection coil's vicinity it will interact with the coil's magnetic field. This interaction may generate signals which are comparable in magnitude to the signals due to objects we wish to detect, thus limiting the maximum detector gain and, correspondingly, the weakest signal and target detectable.

When metallic element is an electronic circuit, parasitic signals may be induced to the coils by the currents in the electronic circuits, especially when switched signals result in magnetic field transients. For example, DC/DC converter circuits may use switched inductors in order to regulate the voltage. A typical architecture may involve deliberately introducing a discontinuity in voltage on an inductor or transformer, with a corresponding switching of the inductor's magnetic field.

Such variations in magnetic field are then picked up as parasitic signals masking the wanted signals.

Moreover, the dynamic nature of the signals—such as its increase and decrease—is often used in detection algorithms. The addition of dynamic parasitic signals may hinder the operation of such algorithms.

Another adverse effect associated with induced currents may be the damaging of components in the electronic circuits. Metal detectors often generate strong switched magnetic fields using their coils, which may induce high voltage levels within the electronic circuits. The high voltages may harm sensitive components within the electronic circuits. Also, signals induced by the metal detector coils may interfere with desired signals within the circuits and harm circuits' performance.

The prior art solutions that are currently used to overcome such problems, rely on magnetic shielding of the electronic circuits and/or system. An example of the magnetic shielding solution is illustrated in US patent application publication number 2013/0057286 to Alexander Lewis Jones et al. entitled "Metal detector sensor head". The disadvantage of applying the shielding disclosed by this publication is that it requires special and expensive materials. Moreover, magnetic shielding increases the weight of the product. Additionally, the shielding provides only a partial solution due to a decline of loss over large bandwidths.

SUMMARY OF INVENTION

According to a first aspect of some embodiments there is provided an apparatus comprising: plurality of electromagnetic coils and a plurality of circuit boards, said circuit boards have planar surface and thickness and wherein at least one of said circuit boards is positioned so that its thickness direction is orthogonal to the magnetic field of at least one of said coils.

In an embodiment, at least one of said plurality of electromagnetic coils is symmetric.

In an embodiment, the planar surface of at least one of said plurality of circuit boards is positioned along a symmetry plane of said at least one electromagnetic coil.

In an embodiment, the thickness direction of said plurality of circuit boards is orthogonal to the magnetic field of at least two electromagnetic coils of said plurality of coils.

In an embodiment, at least one of the plurality of circuit boards comprises electronic circuits associated with, (e.g. connected to) or are part of a metal detector.

In an embodiment, the plurality of said circuit boards comprises circuits associated with, (e.g. connected to) or are part of a radar detector.

In an embodiment, at least two circuit boards of said plurality of circuit boards are positioned so that their thickness direction is orthogonal to the magnetic field of said at least one coil.

In an embodiment, at least one coil is symmetric and wherein said at least one coil comprises more than one symmetry plane, and wherein the planar surface of at least two circuit boards of said plurality of circuits boards is substantially along different symmetry planes of said coil.

In an embodiment, the apparatus comprises a detector module said detector module is selected from the group consisting of: (a) metal detector (b) induction heater (c) noncontact power transfer apparatus (d) noncontact flaw detector.

In an embodiment, said circuit boards are printed circuit boards (PCBs).

According to a second aspect of the invention there is provided a method for collocating electromagnetic coils and circuit boards in a detector, said circuit boards have planar surface and thickness, the method comprising: placing at least one of said circuit boards so that its thickness direction is orthogonal to the magnetic field of at least one of said electromagnetic coils.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks, according to embodiments of the invention, could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein, are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The subject matter disclosed may best be understood by reference to the following detailed description when read with the accompanying drawings in which.

DETAILED DESCRIPTION

Figure 1:
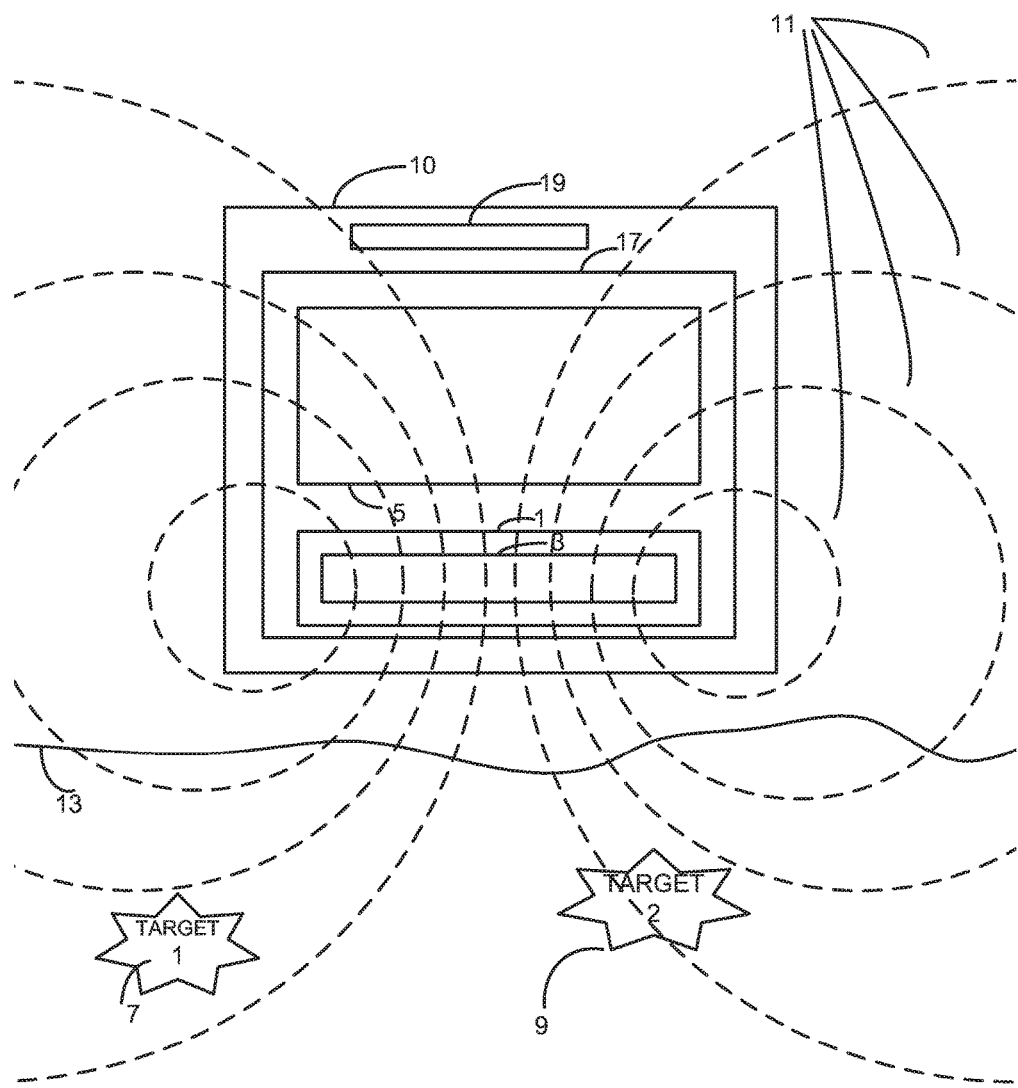
FIG. 1 shows a schematic view of an inductive apparatus according to some embodiments of the invention.

The present invention relates to methods and apparatus for optimizing systems with electromagnetic coils and circuit boards, such as metal detectors, and more specifically, but not exclusively, to methods and apparatus for optimizing the system's dynamic range and reducing interference.

The configurations disclosed herein can be combined in one or more of many ways to provide improved inductive methods and apparatus.

An inductive apparatus such as a metal detector described herein can be augmented with additional sensors to detect nonmetallic objects such as nonmetallic landmines, plastic pipes in a wall, foreign objects in food, and so on.

In one embodiment, a metal or mine detector is combined with a ground penetrating radar (GPR) so as to allow the combined instrument to detect nonmetallic objects/mines as well.

Circuit boards are characterized by being narrow/thin in one dimension (defined herein as "thickness"), and one or more conductors running primarily on the plane defined by the other two lateral dimensions (defined herein as "planar surface"). Circuit boards may contain several layers such as metal layers, and in all of those layers the conductors extend predominantly laterally.

Electronic circuits are commonly implemented on printed circuit boards (PCB). In some cases, antennas (e.g. GPR antennas) such as micro-strip, bow-tie or Vivaldi antennas may also be implemented using PCB technology (e.g. "antenna PCB").

As used herein, the term "Electronic circuits" encompasses PCB or antenna PCB.

An apparatus comprising inductive units or an apparatus such as magnetic metal detector may comprise multiple coils and circuit boards such as electronic printed circuit boards (PCBs). The presence of these circuit boards, while containing metallic traces and layers, may hinder the operation of the metal detector. Thus, according to some embodiments there are provided methods and apparatus for reducing or eliminating the circuit boards effect on the metal detector's coils by positioning the circuit boards in an orientation which significantly reduces or eliminates the interaction between them.

In some cases, the circuit boards may be positioned in an orientation that it faces the detector coil's magnetic field with its narrow/thin side/dimension (thickness), so that essentially there is no "loop area", which is the dominant parameter affecting the interaction between them.

Other than reducing the effect of the circuit boards on the metal detector coils, there are provided methods and apparatus which reduce the stray voltages induced in the circuit boards, due to the magnetic field generated by the coils, which may affect their operation or even damage them.

In some instances, the elements include multiple coils and multiple circuit boards attached to one another in various combinations and the present invention provides methods and apparatus for positioning the circuit boards and or the coils in an orientation which reduces or eliminates the interaction between them.

FIG. 1 is a schematic illustration of an inductive apparatus 10 (e.g. a detector) for detecting objects in accordance with embodiments. Apparatus 10 is configured to detect targets such as metal or nonmetallic inclusions hidden within objects for example metal or nonmetallic objects 7 and 9 buried underground or in mines. According to some embodiments, the apparatus 10 includes one or more detectors such as magnetic detector 1 which includes a magnetic field transmitter and a magnetic field receiver. In some embodiments as illustrated in FIGS. 2 and 3 the magnetic field transmitter and the magnetic field receiver are the same entity including one or more coils 3 generating the magnetic field 11.

According to some embodiments of the invention, the magnetic metal detectors are augmented with additional detection mechanisms. For example a mine sweeping system based on a metal detector may be augmented with a Ground Penetrating Radar [GPR] 5 for detecting non-metallic landmines. In some embodiments both, the metal detector and the GPR are positioned in the apparatus detector head 17.

Apparatus 10 further includes one or more processors 19 for analyzing and processing data such as the data provided by the detectors 5 and 1. In operation, the apparatus 10 is moved, or swept, near the surface of ground 13, while the detector coils and the GPR antennas emit electromagnetic energy into the ground to detect targets 7 and 9.

Since both the metal detector 1 and the GPR 5 should preferably be in proximity to the ground 13, there is a need to place the GPR 5 electronic circuitry in proximity to the coils 3 of the metal detector. Adding electronic circuitry, for example the GPR's electronic circuitry, amidst the coils mentioned above, may have adverse effects on the metal detection operation.

Additionally, the ground 13 may be magnetic, or contain other undesirable electrically conductive objects which, when excited by the transmitted magnetic field, may generate an interfering magnetic field. In order to have some chance of consistently detecting small targets underground, such as a metal target 7 or nonmetallic target 9, in a variety of environments, the apparatus 10 should have excellent rejection of ground mineralization, large dynamic range in the receive electronics, and emit strong high-frequency signals.

Figure 2A:
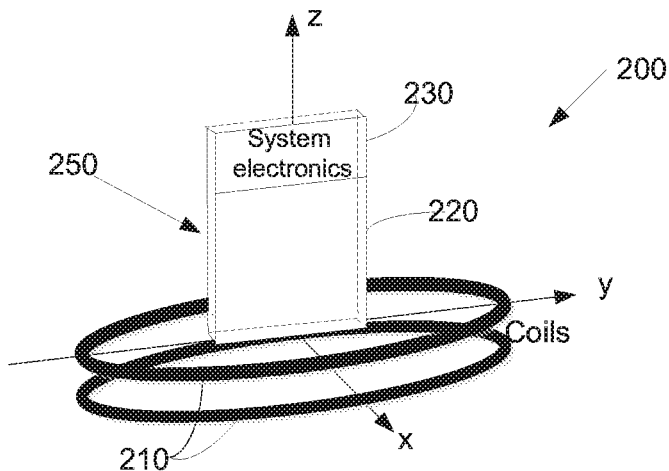
FIGS. 2A and 2B show an isometric view and a top view of an apparatus according to some embodiments of the invention.
Figure 2B:
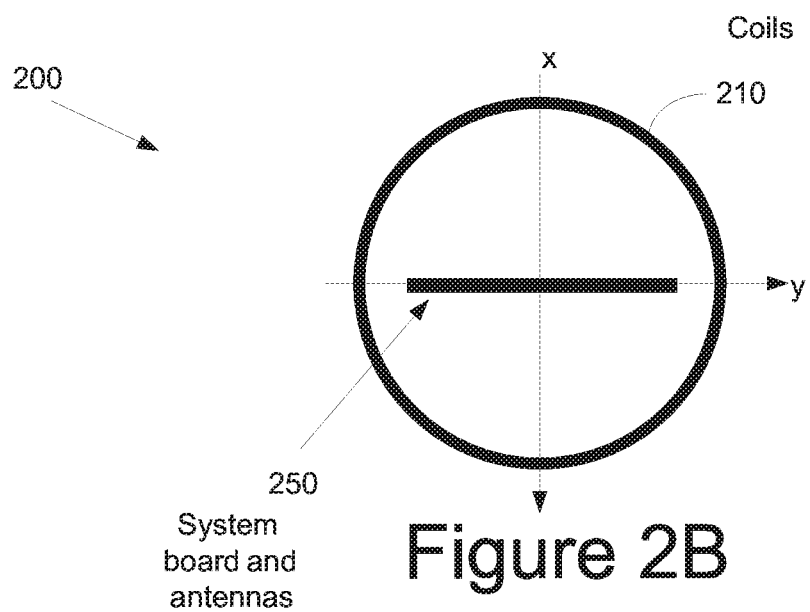

FIGS. 2A and 2B show an isometric view and a top view, respectively, of an apparatus 200 according to some embodiments of the invention. Apparatus 200 comprises one or more coils such as electromagnetic coils 210 positioned perpendicularly to one or more circuit boards such as PCBs 250. For example, according to one embodiment the coils 210 are positioned parallel to a referential Y-X plane in respect to a Cartesian coordinate system (X-Y-Z) that is illustrated in FIG. 2. In an embodiment, the circuit boards are positioned along the referential Y-Z plane, which is a symmetry plane of the coil(s) 210, and the thickness direction of the circuit boards is along the X axis direction. It is noted that according to embodiments of the invention the circuit boards 250 may be positioned along any of the symmetry planes of the coils, e.g. along Y-Z plane or X-Z plane.

Figure 2C:
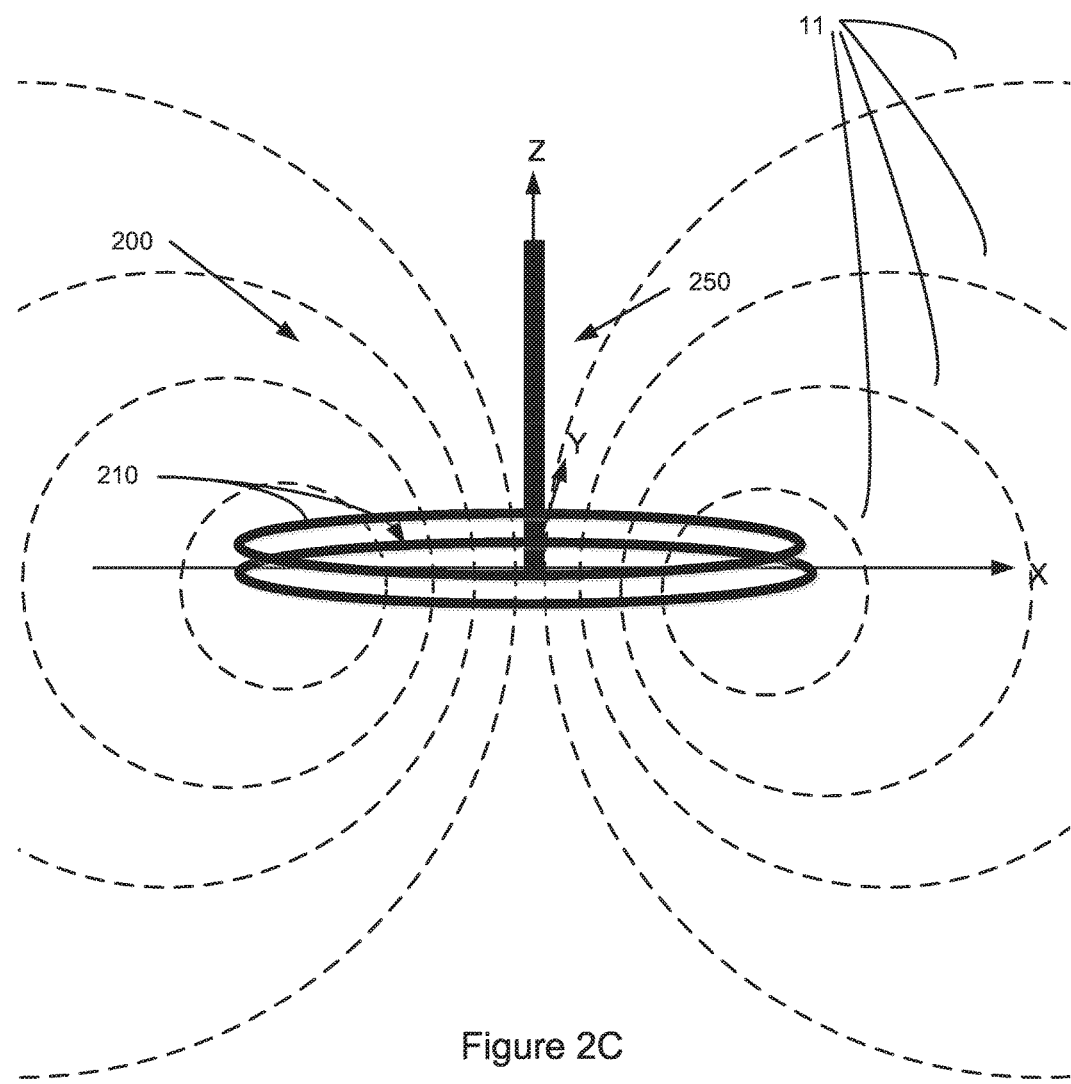
FIG. 2C is a cross section view illustrating the apparatus and the magnetic field according to some embodiments of the invention.

FIG. 2C is cross section view of the apparatus 200 wherein the circuit boards 250 are positioned along the Y-Z plane in respect to a Cartesian coordinate system (X-Y-Z) and wherein the circuit boards thickness direction (X axis) is so that it is orthogonal to the magnetic field 11 of at least one of the coils 210.

As used herein the term "orthogonal", means "orthogonal to within practical limit", such as few degrees, for example up to 5 degrees. For example, if two circuit boards are placed in close proximity parallel to each other, and both are close to the symmetry plane of a coil, then the coil magnetic field is not strictly orthogonal to the thickness direction of each of the circuit boards, but they are close to it within a practical limit. Moreover, if the direction of magnetic field varies along the circuit boards, the intent is that the circuit boards thickness direction is close to being orthogonal to the magnetic field anywhere on the circuit boards.

The one or more electromagnetic coils are electrical conductors such as wires in the shape of a coil, spiral or helix and are preferably symmetric. Typical shape of a coil can be rectangular or circular. Rectangular coils have two symmetry planes, while circular coils have an infinite number of symmetry planes, containing its axis. Coils of a metal detector can be about 10-15 centimeters in size, but can also be smaller (e.g. few centimeters) or larger (e.g. tens of centimeters) depending on size of objects to be detected and distance to them.

The circuit boards 250 may include one or more circuit boards situated along the symmetry plane of coil(s) 210. In the example of the GPR, the circuit boards can be electronic PCBs 230 or antenna PCBs 220.

In some cases, the electronic PCBs comprise the electronics of a detector such as a metal detector for detecting the presence of metal nearby, for example, for finding metal inclusions hidden within objects, or metal objects buried underground.

The apparatus 200 can further comprise a mechanical structure to affix the coils to the circuit boards in a determined physical position. The mechanical structure can facilitate placement and removal of the circuit boards and the coils. The mechanical structure can position the circuit boards and the coils such that they are orthogonal to one another. In some cases, the mechanical structure can comprise one or more of a protrusion, a rim, a flange or a recess. In some cases, a locking mechanism can further couple the coils and the circuit boards. A user can release the locking mechanism to remove the coils from the circuit boards. In many instances, a locking mechanism can be a pin and tumbler locking mechanism.

Figure 3A:
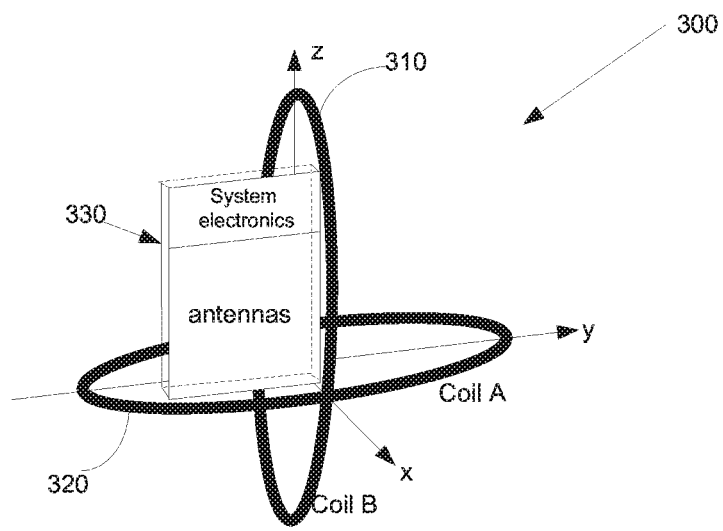
FIGS. 3A and 3B, show an isometric view and a top view of an apparatus comprising two orthogonal coils according to some embodiments of the invention.
Figure 3B:
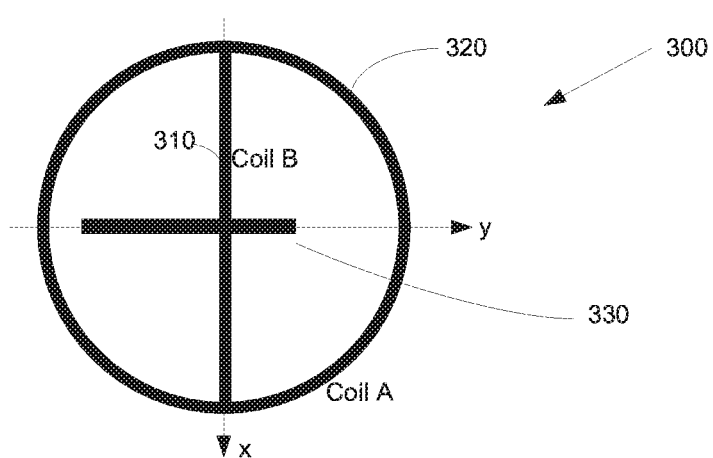

In some examples, the apparatus includes two non-parallel coils surrounding the circuit boards. This is illustrated in FIGS. 3A and 3B, which show a side view and a top view of an apparatus 300 comprising two orthogonal coils 310 and 320 and the circuit boards, in accordance with examples of the invention.

It is stressed that the present invention embodiments applies to any coils orientation as long as the net projected inductive cross-section is minimized. For example, as illustrated in FIGS. 3A and 3B, the two perpendicular coils 310 and 320 are perpendicular to the circuit boards 330, where the circuit boards are positioned along plane Z-Y, coil 320 is positioned along plane Y-X and coil 310 along plane Z-X in respect to Cartesian coordinate system X-Y-Z.

Figure 4A:
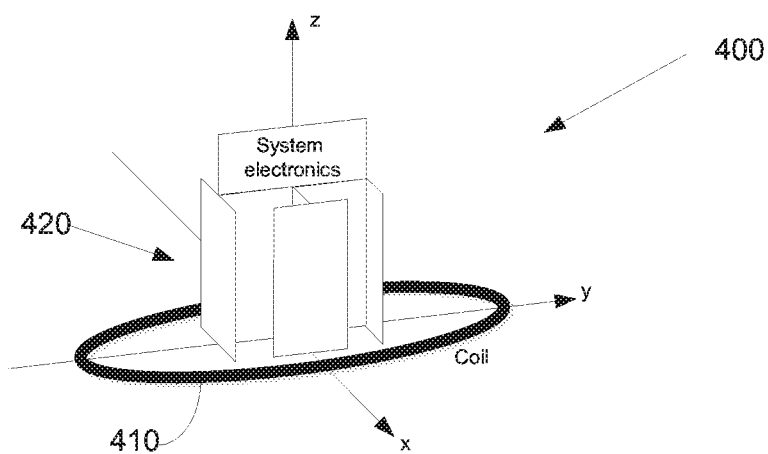
FIGS. 4A and 4B show an isometric view and a top view of an apparatus including a single electromagnetic coil and an antenna array with no closed loops, according to some embodiments of the invention.
Figure 4B:
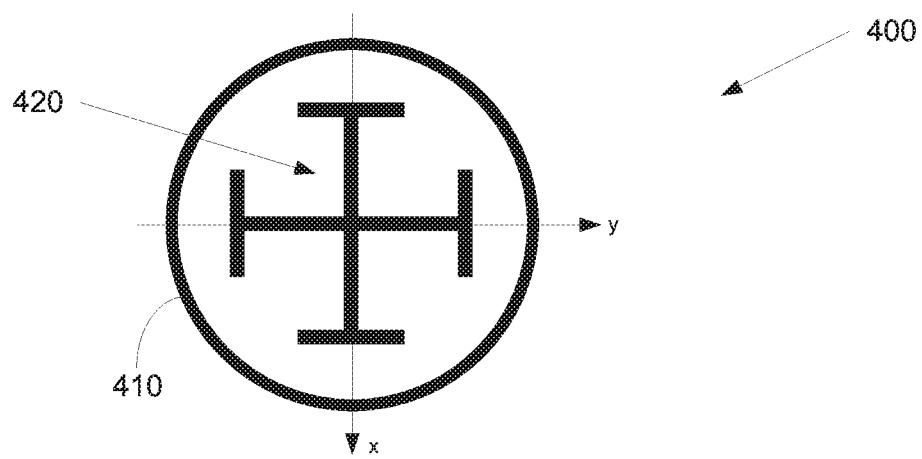

FIGS. 4A and 4B show a side view and a top view of an apparatus 400 including a single electromagnetic coil 410 and an antenna array 420 such as an antenna array with no closed loops, in accordance with embodiments of the invention.

In the example of FIG. 4 the coil 410 is positioned along Y-X plane in respect to Cartesian coordinate system X-Y-Z, orthogonal to antenna array 420.

In some cases, the antenna array is 'cross' shaped orthogonal to the coil 410. In the example of FIG. 4, there are two circuit boards situated at two different symmetry planes of coil 410, and four smaller circuit boards (antenna PCBs) which are off-center by a distance which still keeps them essentially along the direction of the coil's magnetic field. For example, the above mentioned antenna PCBs can be parallel to the coil's magnetic field up to a difference of 5 degrees.

In some cases, the apparatus comprises a single symmetric coil having more than one symmetry plane, and at least two circuit boards where the planar surfaces of the circuit boards are essentially along different symmetry planes of the coil.

In some cases the apparatus, such as apparatus 100 is a metal detector or an induction heater or a noncontact power transfer apparatus or a noncontact charger.

It is stressed that the present invention is related to metal detectors, but may be applicable to other systems, such as induction heating systems or noncontact charging systems or noncontact flaw detector.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only. The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An apparatus comprising:
a plurality of electromagnetic coils and a plurality of circuit boards, said circuit boards have a planar surface and a thickness extending in a thickness direction orthogonal to said planar surface, said plurality of electromagnetic coils being positioned parallel to a referential plane,
wherein at least one of said plurality of electromagnetic coils has at least one symmetry plane perpendicular to said referential plane, and
wherein the planar surface of at least one of said plurality of circuit boards is positioned along one of said at least one symmetry plane of said at least one of said plurality of electromagnetic coils, so that the thickness direction of said at least one of said plurality of circuit boards is orthogonal to the magnetic field of said at least one of said plurality of electromagnetic coils.

2. The apparatus of claim 1, wherein at least two of said plurality of electromagnetic coils have a common symmetry plane perpendicular to said referential plane, and wherein the planar surface of at least one of said plurality of circuit boards is positioned along said common symmetry plane of said at least two electromagnetic coils, so that the thickness direction of said at least one of said circuit board is orthogonal to the magnetic field of said at least two of said coils.

3. The apparatus of claim 1, wherein at least one of said plurality of circuit boards comprises electronic circuits configured to be connected to or are part of a metal detector.

4. The apparatus of claim 1, wherein at least one of said plurality of said circuit boards comprises circuits configured to be connected to, or are part of a radar detector.

5. The apparatus of claim 1, wherein the planar surface of at least two of said plurality of circuit boards are each positioned along the at least one symmetry plane of said at least one electromagnetic coil, so that the thickness direction of each of said at least two of said circuit boards is orthogonal to the magnetic field of said at least one of said electromagnetic coils.

6. The apparatus of claim 5, wherein said at least one coil comprises more than one symmetry plane, and wherein the planar surface of at least two circuit boards of said plurality of circuits boards is substantially along different symmetry planes of said coil.

7. The apparatus of claim 1, wherein the apparatus comprises a detector module said detector module is selected from the group consisting of: (a) metal detector (b) induction heater (c) noncontact power transfer apparatus (d) noncontact flaw detector.

8. The apparatus of claim 1, wherein said circuit boards are printed circuit boards (PCBs).

9. A method for collocating a plurality of electromagnetic coils and a plurality of circuit boards in a detector, said plurality of circuit boards have a planar surface and a thickness extending in a thickness direction orthogonal to said planar surface, said plurality of electromagnetic coils being positioned parallel to a referential plane, and wherein at least one of said plurality of electromagnetic coils has at least one symmetry plane perpendicular to said referential plane, the method comprising:
placing the planar surface of at least one of said circuit boards along one of said at least one symmetry plane of said at least one of said plurality of electromagnetic coils so that the thickness direction of said at least one of said plurality of circuit boards is orthogonal to the magnetic field of said at least one of said plurality of electromagnetic coils.

10. The method of claim 9, wherein at least two of said plurality of electromagnetic coils have a common symmetry plane perpendicular to said referential plane, and wherein the planar surface of at least one of said plurality of circuit boards is positioned along said common symmetry plane of said at least two electromagnetic coils, so that the thickness direction of said at least one of said circuit board is orthogonal to the magnetic field of said at least two of said coils.

11. The method of claim 9, wherein at least one of said plurality of circuit boards comprises electronic circuits configured to be connected to or are part of a metal detector.

12. The method of claim 9, wherein at least one of said plurality of said circuit boards comprises circuits configured to be connected to, or are part of a radar detector.

13. The method of claim 9, wherein the planar surface of at least two of said plurality of circuit boards are each positioned along the at least one symmetry plane of said at least one electromagnetic coil, so that the thickness direction of each of said at least two of said circuit boards is orthogonal to the magnetic field of said at least one of said electromagnetic coils.

14. The method of claim 13, wherein said at least one coil comprises more than one symmetry plane, and wherein the planar surface of at least two circuit boards of said plurality of circuits boards is substantially along different symmetry planes of said coil.

15. The method of claim 9, wherein the detector is selected from the group consisting of: (a) metal detector (b) induction heater (c) noncontact power transfer apparatus (d) noncontact flaw detector.

16. The method of claim 9, wherein said circuit boards are printed circuit boards (PCBs).

* * * * *